United States Patent [19]

Cölln et al.

[11] 4,067,970
[45] Jan. 10, 1978

[54] PESTICIDAL O-ETHYL-S-n-PROPYL-O[PYRAZOLIO(1,5-a)-PYRIMIDIN-(2) YL]-THIONOTHIOLPHOSPHORIC ACID ESTERS

[75] Inventors: Reimer Cölln; Hans-Jochem Riebel, both of Wuppertal; Ingeborg Hammann, Cologne; Bernhard Homeyer, Leverkusen, all of Germany

[73] Assignee: Bayer Aktiengesellschaft, Leverkusen, Germany

[21] Appl. No.: 727,203

[22] Filed: Sept. 27, 1976

[30] Foreign Application Priority Data

Oct. 14, 1975 Germany .............................. 2545881

[51] Int. Cl.$^2$ ...................... A01N 9/36; C07D 239/00
[52] U.S. Cl. ................. 424/200; 260/256.5 R
[58] Field of Search ................. 424/200; 260/256.5 R

[56] References Cited

U.S. PATENT DOCUMENTS

| | | | |
|---|---|---|---|
| 3,402,176 | 9/1968 | Schicke | 424/200 X |
| 3,478,029 | 11/1969 | Schicke | 424/200 X |
| 3,761,479 | 9/1973 | Hoffman et al. | 424/200 X |
| 3,840,541 | 10/1974 | Cölln et al. | 424/200 X |
| 3,950,337 | 4/1976 | Hoffman et al. | 424/200 X |
| 3,966,730 | 6/1976 | Hofer et al. | 424/200 X |
| 3,992,399 | 11/1976 | Böhner et al. | 424/200 X |

Primary Examiner—Leonard Schenkman
Attorney, Agent, or Firm—Burgess, Dinklage & Sprung

[57] ABSTRACT

O-Ethyl-S-n-propyl-O-[pyrazolo(1,5a)-pyrimidin(2)-yl]-thionothiolphosphoric acid esters of the formula $$\underset{n-C_3H_7S}{\overset{C_2H_5O}{\diagdown}}\overset{S}{\underset{\|}{P}}-O-\text{[pyrazolo-pyrimidine with substituents } R, R_1, R_2, R_3\text{]} \quad (I)$$

in which
R is hydrogen or halogen,
$R_1$ is alkyl with 1 to 5 carbon atoms or hydrogen,
$R_2$ is hydrogen, halogen or acetyl, and
$R_3$ is hydrogen, alkyl with 1 to 4 carbon atoms or carbalkoxy with 1 to 4 carbon atoms in the alkyl radical,
which possess arthropodicidal and nematicidal properties.

10 Claims, No Drawings

PESTICIDAL O-ETHYL-S-N-PROPYL-O[PYRAZOLO(1,5-A)-PYRIMIDIN-(2)YL]-THIONOTHIOLPHOSPHORIC ACID ESTERS

The present invention relates to and has for its objects the provision of particular new O-ethyl-S-n-propyl-O-[pyrazolo(1,5-a)-pyrimidin(2)yl]-thionothiolphosphoric acid esters which possess arthropodicidal and nematicidal properties, active compositions in the form of mixtures of such compounds with solid and liquid dispersible carrier vehicles, and methods for producing such compounds and for using such compounds in a new way especailly for combating pests, e.g. insects, acarids and nematodes, with other and further objects becoming apparent from a study of the within specification and accompanying examples.

It is known from Belgian Pat. Specifications 676,802 and 681,814 and U.S. Pat. No. 3,950,337 that O-pyrazolopyrimidinethionophosphoric acid esters, such as, for example, O,O-diethyl-O-[5,7-dimethyl- (Compound A) and-[5-methylpyrazolo-(1,5-a)-pyrimidin(2-)yl]- (Compound B) or O,O-diethyl-O-[6-chloro-5,7-dimethylpyrazolo(1,5-a)-pyrimidin(2)yl]-thionophosphoric acid ester (Compound C), exhibit a pesticidal, especially insecticidal and acaricidal action.

The present invention now provides, as new compounds, the O-pyrazolopyrimidinethionothiolphosphoric acid esters of the general formula

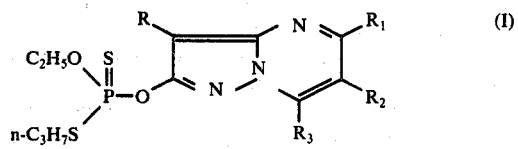

in which
R is hydrogen or halogen,
$R_1$ is alkyl with 1 to 5 carbon atoms or hydrogen,
$R_2$ is hydrogen, halogen or acetyl, and
$R_3$ is hydrogen, alkyl with 1 to 4 carbon atoms or carbalkoxy with 1 to 4 carbon atoms in the alkyl radical.

Preferably, R represents hydrogen, chlorine or bromine, $R_1$ represents hydrogen or straight-chain or branched alkyl with 1 to 4 carbon atoms, $R_2$ represents hydrogen, chlorine or acetyl and $R_3$ represents hydrogen or straight-chain or branched alkyl with 1 to 3 carbon atoms or straight-chain or branched carbalkoxy with 1 to 3 carbon atoms in the alkyl radical.

Surprisingly, the O-pyrazolopyrimidinethionothiolphosphoric acid esters according to the invention exhibit a substantially greater insecticidal, acaricidal and nematicidal action, with a low toxicity to warm-blooded animals, than the previously known compounds of analogous structure and of the same type of action. The compounds according to the invention thus represent a genuine enrichment of the art.

The present invention also provides a process for the preparation of an O-pyrazolopyrimidinethionothiolphosphoric acid ester of the formula (I), in which an O-ethyl-S-n-propylthionothiolphosphoric acid diester halide of the general formula

in which
Hal represents halogen, preferably chlorine or bromine, is reacted with a 2-hydroxypyrazolopyrimidine derivative of the general formula

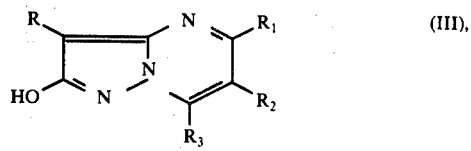

in which
R to $R_3$ have the above-mentioned meanings, the latter being employed as such, in the presence of an acid acceptor, or in the form of an alkali metal salt, alkaline earth metal salt or ammonium salt.

If O-ethyl-S-n-propylthionothiolphosphoric acid diester chloride and 2-hydroxy-5-methyl-pyrazolo(1,5-a)-pyrimidine are used as starting materials, the course of the reaction can be represented by the following equation:

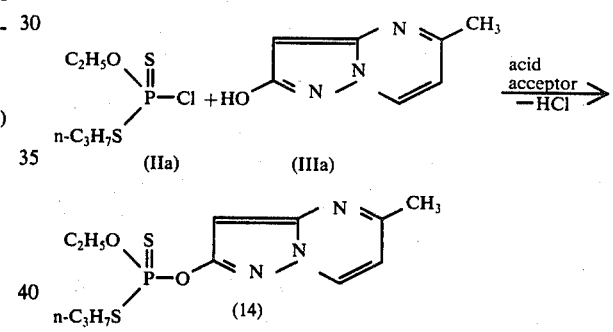

The O-ethyl-S-n-propylthionothiolphosphoric acid diester halide to be used as the starting material is disclosed in U.S.S.R. Pat. No. 184,863 and pyrazolopyrimidine derivatives have been described in the literature and can be prepared in accordance with customary processes according to U.S. Pat. Nos. 3,840,541 and 3,761,479 and published Netherlands Patent Application 6,607,675.

The following may be mentioned as individual examples of the above: 2-hydroxy-pyrazolo(1,5-a)-pyrimidine, and 3-chloro-, 3-bromo-, 5-methyl-, 5-ethyl-, 5-n-propyl-, 5-isopropyl-, 5-n-butyl-, 5-sec.-butyl-, 5-isobutyl-, 5-tert.-butyl-, 6-acetyl-, 7-methyl-, 7-ethyl-, 7-n-propyl-, 7-isopropyl-, 7-carbomethoxy-, 7-carbethoxy-, 7-carbo-n- propoxy-, 7-carbo-isopropoxy-, 5,7-dimethyl-, 5,7-diethyl-, 5,7-di-n-propyl-, 5-methyl-7-carbomethoxy-, 5-methyl-7-carbethoxy-, 5-ethyl-7-carbomethoxy-, 5-ethyl-7-carbethoxy-, 5-n-propyl-7-carbethoxy-, 5-isopropyl-7-carbethoxy-, 5-n-butyl-7-carbethoxy-, 5-isobutyl-7-carbethoxy-, 5-sec.-butyl-7-carbethoxy-, 5-tert.-butyl-7-carbethoxy-, 6-acetyl-7-methyl, 6-chloro-5,7-dimethyl-, 6-chloro-5,7-diethyl-, 3-chloro-7-methyl-, 3-chloro-7-ethyl-, 3-chloro-7-n-propyl-, 3-bromo-7-methyl-, 3-bromo-7-ethyl-, 3-bromo-7-n-propyl-, 3-bromo-6-acetyl-7-methyl-, 3-bromo-6-acetyl-7-ethyl-, 3-bromo-6-chloro-5,7-dimethyl-, 3,6-dichloro- 5,7-dimethyl-, 3-chloro-5-methyl-, 3-chloro-5-ethyl-, 3-bromo-5-methyl- and 3-bromo-5-ethyl-2-hydroxypyrazolo(1,5-a)-pyrimidine.

The preparative process is preferably carried out in the presence of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example, acetone, methyl ethyl ketone, methyl isopropyl ketone and methyl isobutyl ketone; nitriles, for example acetonitrile and propionitrile; and formamides, especially dimethylformamide.

All customary acid-binding agents can be used as acid acceptors. Alkali metal carbonates and alkali metal alcoholates, such as sodium carbonate or potassium carbonate, sodium methylate and ethylate or potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, temperatures of between 0° and 100° C, preferably from 15° to 35° C, are used. The reaction is in general carried out under normal pressure.

To carry out the process, the starting materials are in most cases employed in equimolar amounts. An excess of one or other reactant produces no significant advantages. The reaction is preferably carried out in the presence of one of the above-mentioned solvents and in the presence of an acid acceptor, at the stated temperatures; after stirring for from one to several hours at the stated temperatures, the reaction mixture is worked up by adding ice water to it. Either the product hereupon directly precipitates in a solid form and is filtered off, washed and recrystallized is appropriate, or the mixture is extracted with an organic solvent, for example toluene. After washing and drying the extract, the solvent is distilled off.

The compounds according to the invention are mostly obtained in a crystalline form and are characterized by their melting points. However, if they are obtained in the form of mostly slightly colored oils, which cannot be distilled without decomposition, then these oils may be freed from the last volatile constituents by so-called "slight distillation," that is to say prolonged heating under reduced pressure to moderately elevated temperatures, and are purified in this way. In that case, they are characterized by their refractive indexes.

As already mentioned, the new O-pyrazolopyrimidinethionothiolphosphoric acid esters are distinguished by an excellent insecticidal, acaricidal and nematicidal activity. They are active against plant pests, pests harmful to health and pests of stored products and some of them also show an action in the veterinary medicine field. They possess a good action against both sucking and biting insects and against mites (Acarina).

For these reasons, the products according to the invention are employed successfully as pesticides in plant protection, hygiene protection and protection of stored products, and also in the veterinary field.

The active compounds are well tolerated by plants, have a favorable level of toxicity to warm-blooded animals, and can be used for combating arthropod pests, especially insects, arachnids and nematodes which are encountered in agriculture, in forestry, in the protection of stored products and of materials, and in the hygiene field. They are active against normally sensitive and resistant species and against all or some stages of development.

The above-mentioned pests include: from the class of the Isopoda, for example *Oniscus asellus, Armadillidium vulgare* and *Porcellio scaber;* from the class of the Diplopoda, for example *Blaniulus guttulatus;* from the order of the Chilopoda, for example *Geophilus carpophagus* and *Scutigera* spec.; from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria* migratorioides, *Melanoplus differentialis* and *Schistocerca gregaria;* from the order of the Dermaptera, for example *Forficula auricularia;* from the order of the Isoptera, for example, *Reticulitermes* spp.; from the order of the Anoplura, for example *Phylloxera vastatrix, Pemphigus* spp., *Pediculus humanus* corporis, Haematopinus spp. and *Linognathus* spp.; from the order of the Mallophaga, for example *Trichlodectes* spp. and *Damalinea* spp.; from the order of the Thysanoptera, for example *Hercinothrips femoralis* and *Thrips tabaci;* from the order of the Heteroptera, for example, Eurygaster spp. *Dysdercus intermedius, Piesma quadrata, Cimex lectularius, Rhodnius prolixus* and *Triatoma* spp.; from the order of the Homoptera, for example *Aleurodes brassicae, Bemisia tabaci, trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius* obtectus, *Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium,* spp., *Tenebrio molitor, Agriotes* spp., *Conoderus* spp., *Melolontha melolontha, Amphimallon solstitialis* and *Costelytra zealandica;* from the order of the *Hymenoptera,* for example *Diprion* spp., *Hoplocampa* spp., *Lasius* spp., *Monomorium pharaonis* and *Vespa* spp.; from the order of the *Diptera*, for example *Aedes* spp., *Anopheles* spp., *Culex* spp., *Drosophila melanogaster*, *Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus*, *Oscinella frit*, *Phorbia* spp., *Pegomyia hyoscyami*, *Ceratitis capitata*, *Dacus oleae* and *Tipula paludosa*; from the order of the *Siphonaptera*, for example, *Xenopsylla cheopis* and *Ceratophyllus* spp.; from the class of the *Arachnida*, for example *Scorpio maurus* and *Latrodectus mactans*; from the order of the Acarina, for example *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* Ixodes spp., *Psoroptes* spp., *Chorioptes* spp., *Sarcoptes* spp., *Tarsonemus* spp., *Bryobia praetiosa*, *Panonychus* spp., and *Tetranychus* spp.

The plant-parasitic nematodes include *Pratylenchus* spp., *Radophlus similis*, *Ditylenchus dipsaci*, *Tuylenchulus semipenetrans*, *Heterodera* spp., *Meloidogyne* spp., *Aphelenchoides* spp., *Longidorus* spp., *Xiphinema* spp. and *Trichodorus* spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers, of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dye-stuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0000001-100, preferably 0.01-10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.00001–95%, and preferably 0.01–95%, by weight of the mixture.

When used against nematodes, the preparations are generally applied to an area of agriculture in amounts of 1 to 100 kg of active compound per hectare, and are then incorporated into the soil.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance along, e.g. about 20–100% by weight of the active compound.

Furthermore, the present invention contemplates methods of selectively killing, combating or controlling pests, e.g. arthropods, especially insects and acarids, and nematodes, which comprises applying to at least one of correspondingly (a) such arthropods, (b) such nematodes, and (c) the corresponding habitat thereof, i.e. the locus to be protected, e.g. to a growing crop, to an area where a crop is to be grown or to a domestic animal, a correspondingly combative or toxic amount, i.e. an arthropodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Drosophila test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier, and the concentrate was diluted with water to the desired concentration.

1 cm³ of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed; 0% means that no flies were killed.

The active compounds, the concentrations of the active compounds, the evaluation times and the results can be seen from the following table:

Table 1

(*Drosophila* test)

| Active compound | Active compound concentration in % | Degree of destruction in % after 1 day |
|---|---|---|
| (known) (A) | 0.1 | 0 |
| (known) (C) | 0.1 | 0 |
| (8) | 0.1 | 100 |
| (2) | 0.1 | 100 |
| (3) | 0.1 | 100 |
| (4) | 0.1 | 100 |

Table 1-continued
(Drosophila test)

| Active compound | Active compound concentration in % | Degree of destruction in % after 1 day |
|---|---|---|
| (9) C₂H₅O–P(=S)(–O–...)–S–n-C₃H₇ with pyrazolo-pyrimidine bearing C₂H₅ | 0.1 | 100 |
| (1) C₂H₅O–P(=S)(–O–...)–S–n-C₃H₇ with pyrazolo-pyrimidine bearing CH₃, CH₃ | 0.1 | 100 |

EXAMPLE 2

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 2
(Myzus test)

| Active compound | Active compound concentration in % | Degree of destruction in % after 1 day |
|---|---|---|
| (known) (C) (C₂H₅O)₂P(=S)–O– pyrazolo-pyrimidine with CH₃, Cl, CH₃ | 0.1 / 0.01 | 95 / 40 |
| (2) C₂H₅O–P(=S)(–O–...)–S–n-C₃H₇; CH₃ substituent | 0.1 / 0.01 / 0.001 | 100 / 100 / 100 |
| (9) C₂H₅O–P(=S)(–O–...)–S–n-C₃H₇; C₂H₅ substituent | 0.1 / 0.01 / 0.001 | 100 / 100 / 100 |
| (10) C₂H₅O–P(=S)(–O–...)–S–n-C₃H₇; unsubstituted | 0.1 / 0.01 / 0.001 | 100 / 98 / 95 |
| (11) C₂H₅O–P(=S)(–O–...)–S–n-C₃H₇; Cl substituent | 0.1 / 0.01 / 0.001 | 100 / 95 / 95 |

EXAMPLE 3

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 3

(Tetranychus test)

| Active compound | Active compound concentration in % | Degree of destruction in % after 2 day |
|---|---|---|
| (known) (B): $(C_2H_5O)_2P(=S)-O-$ [pyrazolo-pyrimidine with CH$_3$] | 0.1 | 0 |
| (known) (A): $(C_2H_5O)_2P(=S)-O-$ [pyrazolo-pyrimidine with CH$_3$, CH$_3$] | 0.1 | 0 |
| (known) (C): $(C_2H_5O)_2P(=S)-O-$ [pyrazolo-pyrimidine with CH$_3$, Cl, CH$_3$] | 0.1 | 0 |
| (9): $C_2H_5O-P(=S)(S-n-C_3H_7)-O-$ [pyrazolo-pyrimidine with C$_2$H$_5$] | 0.1 | 90 |
| (10): $C_2H_5O-P(=S)(S-n-C_3H_7)-O-$ [pyrazolo-pyrimidine] | 0.1 / 0.01 | 80 / 50 |

EXAMPLE 4

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which was quoted in ppm (=mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all test insects had been killed and was 0% if exactly as many test insects were still alive as in the case of the untreated control.

The active compounds, amounts used and results can be seen from the table which follows:

Table 4

(Phorbia antiqua grubs in the soil)

| Active compound | Degree of destruction in % at an active compound concentration of 2.5 ppm |
|---|---|
| (known) (A): $(C_2H_5O)_2P(=S)-O-$ [pyrazolo-pyrimidine with CH$_3$, CH$_3$] | 0 |
| (known) (C): $(C_2H_5O)_2P(=S)-O-$ [pyrazolo-pyrimidine with CH$_3$, Cl, CH$_3$] | 0 |
| (known) (B): $(C_2H_5O)_2P(=S)-O-$ [pyrazolo-pyrimidine with CH$_3$] | 0 |
| (9): $C_2H_5O-P(=S)(S-n-C_3H_7)-O-$ [pyrazolo-pyrimidine with C$_2$H$_5$] | 100 |
| (4): $C_2H_5O-P(=S)(S-n-C_3H_7)-O-$ [pyrazolo-pyrimidine with CH$_3$, Cl, CH$_3$] | 100 |

EXAMPLE 5

Test nematode: *Meloidogyne incognita*
Solvent: 3 parts by weight of acetone

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentrations of the active compound in the preparation was of practically no importance; only the amount of active compound per unit volume of soil, which is given hereinafter in ppm (=mg/l), was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

Table 5

| (Meloidogyne incognita) | |
|---|---|
| Active compound | Degree of destruction in % at an active compound concentration of 10 ppm |
| (known) (A) | 0 |
| (known) (C) | 0 |
| (10) | 100 |
| (11) | 100 |
| (9) | 100 |
| (7) | 100 |
| (1) | 100 |

The process of the present invention is illustrated by the following preparative examples:

EXAMPLE 6

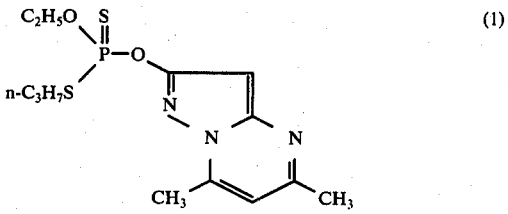

21.4 g (0.1 mole) of O-ethyl-S-n-propyl-thionothiolphosphoric acid diester chloride were added dropwise to a mixture of 16.3 g (0.1 mole) of 2-hydroxy-5,7-dimethylpyrazolo(1,5-a)-pyrimidine, 14.3 g (0.105 mole) of potassium carbonate and 150 ml of dimethylformamide at 20° C. The mixture was allowed to react for a further 2 hours at 20° C and was then poured into ice water. The aqueous solution was extracted three times with 100 ml of toluene at a time and the combined toluene extracts were dried over sodium sulphate and then concentrated. 26 g (75% of theory) of O-ethyl-S-n-propyl-O-[5,7-dimethylpyrazolo(1,5-a)-pyrimidin(2)yl]-thionothiolphosphoric acid ester having a refractive index $n_D^{25}$ of 1.5977 were obtained.

The compounds of the formula

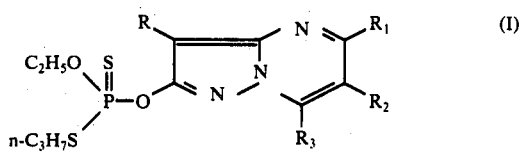 (I)

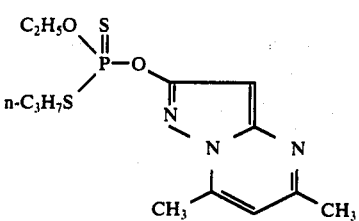

could be prepared analogously:

Table 6

| Compound No. | R  | $R_1$      | $R_2$  | $R_3$         | Yield (% of theory) | Physical data (refractive index; melting point °C) |
|---|---|---|---|---|---|---|
| 2  | H  | H          | CO—CH₃ | —CH₃          | 57 | $n_D^{26}$:1.5978 |
| 3  | Br | H          | CO—CH₃ | —CH₃          | 24 | 90–92 |
| 4  | H  | CH₃        | Cl     | —CH₃          | 60 | $n_D^{21}$:1.5863 |
| 5  | H  | tert.-C₄H₉ | H      | —CO—OC₂H₅     | 33 | $n_D^{21}$:1.5612 |
| 6  | Cl | H          | H      | —C₂H₅         | 94 | 60 |
| 7  | H  | H          | H      | —CH₃          | 67 | 39 |
| 8  | Cl | H          | H      | —CH₃          | 70 | 63.5 |
| 9  | H  | H          | H      | —C₂H₅         | 68 | $n_D^{23}$:1.5785 |
| 10 | H  | H          | H      | H             | 71 | $n_D^{25}$:1.5928 |
| 11 | Cl | H          | H      | H             | 73 | $n_D^{26}$:1.5987 |

Other compounds of formula I which can similarly be prepared include:

Table 7

| Compound No. | R | $R_1$ | $R_2$ | $R_3$ |
|---|---|---|---|---|
| 12 | H | —C₂H₅ | H  | H |
| 13 | H | —CH₃  | H  | H |
| 14 | H | H     | Br | —C₄H₉-sec. |
| 15 | H | H     | H  | —COO—C₄H₉-sec. |
| 16 | H | H     | H  | —C₃H₇-n |
| 17 | H | H     | H  | —COO—C₃H₇-n | and the like.

It will be appreciated that the instant specification and examples are set forth by way of illustration and not limitation, and that various modifications and changes may be made without departing from the spirit and scope of the present invention.

What is claimed is:

1. An O-ethyl-S-n-propyl-O-[pyrazolo(1,5-a)pyrimidin(2)yl]-thionothiolphosphoric acid ester of the formula

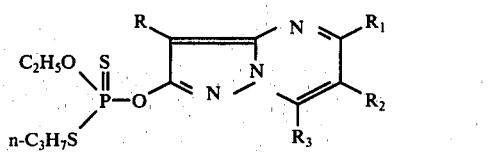

in which
R is hydrogen or halogen,
$R_1$ is hydrogen or alkyl with 1 to 5 carbon atoms,
$R_2$ is hydrogen, halogen or acetyl, and
$R_3$ is hydrogen, alkyl with 1 to 4 carbon atoms or carbalkoxy with 1 to 4 carbon atoms in the alkyl radical.

2. A compound according to claim 1, in which R is hydrogen, chlorine or bromine, $R_1$ is hydrogen or straight-chain or branched alkyl with 1 to 4 carbon atoms, $R_2$ is hydrogen, chlorine or acetyl, and $R_3$ is hydrogen, alkyl with 1 to 3 carbon atoms or carbalkoxy with 1 to 3 carbon atoms in the alkyl radical.

3. The compound according to claim 1 wherein such compound is O-ethyl-S-n-propyl-O-[5,7-dimethylpyrazolo(1,5-a)-pyrimidin(2)yl]-thionothiolphosphoric acid ester of the formula 4. The compound according to claim 1 wherein such compound is O-ethyl-S-n-propyl-O-[6-chloro-5,7-dimethylpyrazolo(1,5-a)-pyrimidin(2)yl]-thionothiolphosphoric acid ester of the formula

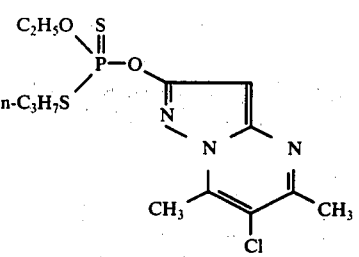

5. The compound according to claim 1 wherein such compound is O-ethyl-S-n-propyl-O-[7-methylpyrazolo(1,5-a)-pyrimidin(2)yl]-thionothiolphosphoric acid ester of the formula

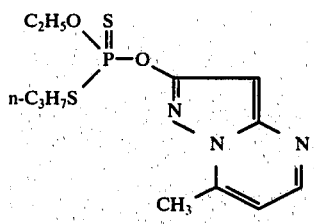

6. The compound according to claim 1 wherein such compound is O-ethyl-S-n-propyl-O-[pyrazolo(1,5-a)-pyrimidin(2)yl]-thionothiolphosphoric acid ester of the formula

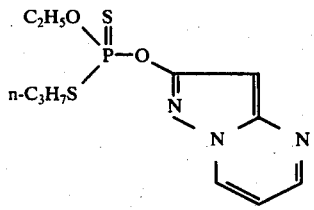

7. The compound according to claim 1 wherein such compound is O-ethyl-S-n-propyl-O-[7-ethylpyrazolo(1,5-a)-pyrimidin(2)yl]-thionothiolphosphoric acid ester of the formula

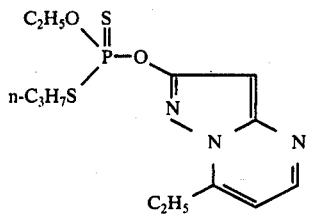

8. A nematicidal or arthropodicidal composition containing as active ingredient a nematicidally or arthropodicidally effective amount of a compound according to claim 1 in admixture with a diluent.

9. A method of combating nematodes or arthropods which comprises applying to the nematodes or arthropods, or to a habitat thereof, a nematicidally or arthropodicidally effective amount of a compound according to claim 1.

10. The method according to claim 9 in which said compound is
O-ethyl-S-n-propyl-O-[5,7-dimethylpyrazolo(1,5-a)-pyrimidin(2)yl]-thionothiolphosphoric acid ester,
O-ethyl-S-n-propyl-O-[6-chloro-5,7-dimethyl-pyrazolo-(1,5-a)-pyrimidin(2)yl]-thionothiolphosphoric acid ester,
O-ethyl-S-n-propyl-O-[7-methylpyrazolo(1,5-a)-pyrimidin(2)yl]-thionothiolphosphoric acid ester,
O-ethyl-S-n-propyl-O-[pyrazolo(1,5-a)-pyrimidin-(2)yl]-thionothiolphosphoric acid ester, or
O-ethyl-S-n-propyl-O-[7-ethylpyrazolo(1,5-a)-pyrimidin(2)yl]-thionothiolphosphoric acid ester.

* * * * *